United States Patent [19]

Tinker et al.

[11] 4,052,461
[45] Oct. 4, 1977

[54] HYDROFORMYLATION PROCESS

[75] Inventors: Harold Burnham Tinker, Zurich, Switzerland; Donald E. Morris, Kirkwood, Mo.

[73] Assignee: Monsanto Company, St. Louis, Mo.

[21] Appl. No.: 565,167

[22] Filed: Apr. 4, 1975

Related U.S. Application Data

[63] Continuation-in-part of Ser. No. 546,227, Feb. 3, 1975, abandoned, and Ser. No. 466,660, March 3, 1974, abandoned, and Ser. No. 310,621, Nov. 29, 1972, abandoned.

[51] Int. Cl.$^2$ .................. C07C 47/48; B01J 21/02
[52] U.S. Cl. ............... 260/599; 260/410.9 R; 260/413; 260/465.1; 260/526 R; 260/561 R; 260/598; 260/601 H; 260/602; 260/604 HF; 560/175; 560/232; 252/432
[58] Field of Search ................ 260/604 HF, 599

[56] References Cited

U.S. PATENT DOCUMENTS

| | | | |
|---|---|---|---|
| 3,527,809 | 9/1970 | Pruett et al. | 260/604 HF |
| 3,547,964 | 12/1970 | Olivier | 260/604 HF X |
| 3,794,671 | 2/1974 | Wilkinson | 260/604 HF X |
| 3,857,867 | 12/1974 | Waspero et al. | 260/604 F X |

FOREIGN PATENT DOCUMENTS

| | | | |
|---|---|---|---|
| 1,361,797 | 4/1964 | France | 260/599 |

OTHER PUBLICATIONS

Cotton et al., Advanced Inorganic Chem., Interscience Publ., pp. 1019-1021 (1966).

*Primary Examiner*—James O. Thomas, Jr.
*Assistant Examiner*—G. T. Breitenstein
*Attorney, Agent, or Firm*—Joseph D. Kennedy; John D. Upham

[57] ABSTRACT

The invention relates to a process for the preparation of aldehydes by the hydroformylation of olefinically unsaturated compounds using a rhodium catalyst which catalyst is provided by (1) introducing rhodium into the reaction solution in the form of an ionic rhodium compound, the said ionic compound consisting of (a) a rhodium-containing cation having rhodium complexed with ligands other than halide, and (b) a non-coordinating anion; and (2) furnishing to the reaction solution at least two moles of a modifying ligand per mole of ionic rhodium compound where the modifying ligand is furnished either pre-coordinated in the said ionic rhodium compound or as a free compound, and where the modifying ligand is a tertiary organo phosphorous compound having from 3 to 90 carbon atoms, or a tertiary organo arsenic compound having from 3 to 90 carbon atoms, or a tertiary organo antimony compound having from 3 to 90 carbon atoms.

The process is especially useful for the production of aldehydes from olefinically unsaturated compounds having from 2 to 30 carbon atoms, carbon monoxide, and hydrogen at a total pressure of from 4.6 to 142 kg/cm$^2$ (50 to 2,000 psig), and at a temperature of from about 60° C to about 180° C.

A preferred embodiment of the invention utilizes the modifying ligand at a molar concentration in excess of that required stoichiometrically by the ionic rhodium compound. Another preferred embodiment of this invention employs the modifying ligand as the solvent for the reaction system.

29 Claims, No Drawings

HYDROFORMYLATION PROCESS

The patent application is a continuation-in-part of Ser. No. 310,621, now abandoned, and 466,660, now abandoned, filed Nov. 29, 1972 and Mar. 3, 1974, respectively, and of Ser. No. 546,227 filed Feb. 3, 1975, now abandoned.

This invention relates to a process for the preparation of aldehydes by hydroformylation of olefinically unsaturated compounds particularly to the catalytic hydroformylation of olefins, such as ethylene, propylene, butylene, pentene or hexene, with hydrogen and carbon monoxide using as catalyst a metal complex provided by ionic coordination complexes of rhodium, to selectively yield the respective aldehyde products, propionaldehyde, butyraldehyde, pentaldehyde, hexaldehyde or heptaldehyde.

Hydroformylation processes are well known in the art and have been directed to the production of reaction mixtures comprising substantial amounts of aldehydes and alcohols by the reaction of olefins with carbon monoxide and hydrogen at elevated temperatures and pressures in the presence of certain catalysts. The prior art teaches the use of dicobaltoctacarbonyl or its various modified forms as well as carbonyls of other Group VIII metals such as rhodium, ruthenium, iridium, etc. which may also be modified by ligands comprised of organic compounds of Group V elements such as triaryl- and trialkyl-phosphines, arsines, etc. Certain disadvantages present in hydroformylation processes described in the prior art are catalyst instability, low levels of catalyst reactivity, and poor product selectivity.

One particular disadvantage of hydroformylation processes of the prior art is their dependence upon the use of catalysts comprised of metal carbonyls or certain modified metal carbonyls including dicobalt-octacarbonyl, tetracarbonyl-cobalt hydride and organo phosphine substituted cobalt carbonyls, which generally necessitate the use of high pressures to remain stable under the high reaction temperatures employed. Dicobalt-octacarbonyl requires a very high partial pressure of carbon monoxide to maintain catalyst stability under hydroformylation conditions. These partial pressures of carbon monoxide are often in excess of 20 kg/cm$^2$ at moderate temperatures in the range of 50° C to 100° C, and range as high as 211 kg/cm$^2$ carbon monoxide partial pressure under normal hydroformylation conditions. Organo phosphine substituted complexes of dicobaltoctacarbonyl are often more stable and therefore require considerably lower partial pressures of carbon monoxide and consequently can be used in a low pressure hydroformylation process. However, even these catalysts are often not stable enough to withstand the severe operating conditions necessary for product isolation and catalyst recovery in the oxo processes and suffer from reduced activity.

Another disadvantage of hydroformylation processes disclosed in the prior art is their dependence on catalyst systems which often require the addition of other compounds such as carboxylic acids as agents to maintain a reactive and stable metal complex catalyst system under reaction and processing conditions necessary for the hydroformylation reactions, product isolation, catalyst recovery and catalyst recycle. For example, the hydroformylation catalyst dicobaltoctacarbonyl is precipitated as cobalt metal during product distillation and, consequently, must be reconverted to the active catalyst in a separate step.

Still another disadvantage of hydroformylation processes disclosed in the prior art is their relatively low level of activity. This low level of activity requires very high catalyst concentrations, long reaction times and high temperatures to obtain substantial reaction rates and conversions. Consequently, very large and costly processing equipment is required.

Another disadvantage of hydroformylation processes disclosed heretofore is their inability to maintain high selectivity to aldehydes at the temperature required for high conversion levels and high reaction rates. At these higher temperatures hydroformylation by-products comprising substantial amounts of alcohols and parrafins are formed. Often undesirable side reactions occur between the desired aldehyde products and by-products, such as the alcohols, resulting in the formation of more and higher-boiling by-products such as acetals and hemiacetals and other condensation products. Consequently, substantially lower selectivity and yield of the desired aldehyde occurs in hydroformylation processes described heretofore. A separate product isolation stage is also necessary to yield substantially pure aldehyde product.

Another disadvantage of hydroformylation processes disclosed in the prior art is their dependence on catalysts (cobalt and rhodium) which frequently isomerize olefins such as 1-hexene, and consequently yield a broad spectrum of branched aldehydes. In addition, neutral (non-ionic) rhodium complexes described in the prior art (e.g. RhClCO(Ph$_3$P)$_2$ or Rh(O$_2$CCH$_3$) CO(Ph$_3$P)$_2$) which do not isomerize olefins yield aldehyde product mixtures in which the normal to branched isomer ratios are substantially less than those obtained with the catalyst system of the present invention. Undesirable side reactions may also occur between the desired aldehyde product and the additional "stabilizing compounds", such as carboxylic acids, leading to the acid catalyzed formation of undesirable high boiling condensation products. A separate product isolation stage is usually necessary to yield substantially pure aldehyde product. Consequently, substantially lower selectivity and yield of aldehyde occurs in hydroformylation processes described hereintofore.

It is, therefore, an object of the present invention to avoid the effects of the above disadvantages and thus provide all improved and more selective and commercially feasible hydroformylation process. Another object of this invention is to provide a highly reactive, highly selective, and highly stable hydroformylation catalyst composition and process. Still another object of the present invention is to provide a selective and reactive hydroformylation catalyst composition and process for the production of aldehydes, while substantially avoiding olefin feedstock isomerization and olefin hydrogenation as well as aldehyde hydrogenation.

Still another object of the present invention is to make available a means of providing a selective and reactive hydroformylation catalyst composition without the use of expensive and dangerous reducing agents such as hydrazine.

Another object of the present invention is to provide a hydroformylation catalyst composition and process which result in production of higher yields of aldehydes with no substantial formation of alcohols and/or paraffins.

Another object of the present invention is to provide a more stable and more reactive hydroformylation catalyst composition and process so that lower carbon monoxide partial pressure and consequently total reactor pressure may be used in the hydroformylation process of this invention than has been heretofore typically employed.

Another object of the present invention is to provide a hydroformylation catalyst composition and process which result in higher yields of aldehyde products comprised predominantly of normal aldehydes from alpha olefins as contrasted to the higher yields of aldehydes with longer side chains as obtained by prior art processes, for example, processes using cobalt catalysts. The unbranched aldehydes, e.g. 1-octanal, are preferred in many industrial applications such as in the manufacture of detergent compositions and plasticizer esters.

Still another object of the present invention is to provide an improved and stable hydroformylation catalyst composition which does not necessitate the use of other compounds, such as carboxylic acids, to maintain its reactivity and stability under reaction and processing conditions of this hydroformylation process. Consequently, the product isolation and catalyst recovery steps, as well as the recycle steps, in the present hydroformylation process are greatly simplified.

Still another object of the present invention is to provide a process employing a hydroformylation catalyst composition which is quite active, yields a high percentage of linear (normal) aldehyde product, and can be conveniently introduced in high concentrations into a hydroformylation reaction vessel in a solution form. Many prior art rhodium compounds, e.g., $RhCl(CO)(Ph_3P)_2$ are only partially soluble in solvents of moderate polarity, e.g. benzene, chloroform, tetrahydrofuran, etc. However, these chloride-containing compounds yield catalyst compositions which have inferior hydroformylation activities and yield lower percentages of linear aldehyde products than the catalysts employed in the present invention. Other prior art rhodium compounds, e.g., $HRh(CO)(Ph_3P)_3$, yield catalyst compositions which have quite low solubilities in solvents of moderate to high polarity, e.g., benzene, chloroform, tetrahydrofuran, acetone, ethanol, acetophenone, dioctyl phthalate, etc. On the other hand ionic rhodium compounds used in the present invention are quite soluble in solvents of moderate to high polarity and yield catalyst compositions which have high hydroformylation activities and yield high percentages of linear aldehyde product. Thus the distinct advantage of introducing the rhodium into a hydroformylation reaction vessel as a highly concentrated solution of small volume is realized through the use of the ionic rhodium compounds employed in the present invention.

Furthermore, in commercial processes, due to the high polarity of the aldehyde products, and the high polarity of high boiling solvents, such as dioctyl phthalate, which are used for recycling the catalyst, the high solubility of catalysts of the present invention is a great advantage over less soluble rhodium-containing catalysts of the prior art.

Still another object of the present invention is the provision of an improved hydroformylation process enabling the efficient single stage production of aldehydes by reaction of olefinic hydrocarbons with carbon monoxide and hydrogen in the presence of an improved and more stable catalyst, enabling the use of lower catalyst concentration, lower temperature, lower pressure, and shorter contact time than generally possible heretofore, and facilitating product isolation, catalyst recovery, and recycle steps without substantial decomposition and loss.

These and other objects of the present invention will become apparent to those skilled in the art from the accompanying description and disclosure.

The present invention is an improved process for the production of aldehydes, by the reaction of an olefinically unsaturated compound having from 2 to 30 carbon atoms, carbon monoxide, and hydrogen, at a total pressure of from 4.6 to 142 kg/cm², at a temperature of from about 60° C to about 180° C, the improvement which comprises contacting the said reactants in the presence of a solution of a rhodium catalyst, in which said catalyst is provided by (1) introducing rhodium into the reaction solution in the form of an ionic rhodium compound, the said ionic compound consisting of (a) a rhodium-containing cation having rhodium complexed with ligands other than halide, and (b) a non-coordinating anion; and (2) furnishing to the reaction solution at least two moles of modifying ligand per mole of ionic rhodium compound where the modifying ligand is furnished either pre-coordinated in the said ionic rhodium compound or as a free compound; and where the modifying ligand is a tertiary organo phosphorus compound having from 3 to 90 carbon atoms, or a tertiary organo arsenic compound having from 3 to 90 carbon atoms, or a tertiary organo antimony compound having from 3 to 90 carbon atoms. Examples of the present rhodium complexes include $[Rh(COD)(Ph_3P)_2]BPh_4$ where COD is 1,5-cyclooctadiene and $[Rh(CO)_3(Ph_3P)_2]BPh_4$, but not rhodium hydrides, e.g. $HRh(CO)(Ph_3P)_3$ since the hydrides are not ionic compounds.

The modifying ligand may be present in stoichiometric proportion as required by the ionic rhodium compound, or preferably in molar excess to the ionic rhodium compound, e.g., a molar concentration of from 0.0001 to 10 molar. More preferred ranges are 0.0001 to 0.001 molar, and 0.001 to 10 molar. Still more preferred ranges are 0.01 to 0.1 molar and 0.1 to 2.5 molar.

In accordance with the present invention, olefinically unsaturated compounds are converted selectively to aldehydes having one more carbon atom than the olefinic compounds by reacting the olefinic compounds with carbon monoxide and hydrogen at temperatures from about 60° C to 180° or preferably 80° C to 130° C, and at a total pressure of from 4.6 kg/cm² to 142 kg/cm² preferably 4.6 to 36 kg/cm², although higher pressures may be employed in the presence of the rhodium catalyst described herein. In carrying out the typical hydroformylation reaction selectively to produce aldehydes it is necessary to supply one mole of carbon monoxide and one mole of hydrogen for each mole of olefin reacted. Excess carbon monoxide or hydrogen over the aforesaid stoichiometric amounts, however, may be present. Any ratio of $H_2$ to CO from 10:1 to 1:10 may be chosen.

The term modifying ligand used throughout this specification means a tertiary organo phosphorus compound, or a tertiary organo arsenic compound, or a tertiary organo antimony compound. This compound is either coordinated to the central rhodium atom to form the cationic coordination complex, or is present as the free compound, i.e., uncoordinated, in the reaction solution containing the rhodium coordination complex. In this latter case compound has the potential to become coordinated to the central rhodium atom via a ligand exchange reaction with a modifying ligand already coordinated to the central rhodium atom.

Suitable organo phosphorus, organo arsenic, and organo antimony modifying ligands which may comprise part of the ionic rhodium coordination compound of this invention are those containing trivalent phosphorus, arsenic, or antimony atoms, and are referred to in this specification as phosphines and phosphites, arsines and arsenites, and stibines and stibites, respectively.

In this group of suitable modifying ligands, the individual phosphorus, arsenic, and antimony atoms have one available or unshared pair of electrons. An organic derivative of the phosphorus, arsenic, or antimony with the foregoing electronic configuration is, therefore, a suitable ligand for the rhodium containing catalyst of this invention. Organic radicals of any size and composition may be bonded to the phosphorus, arsenic, or antimony atoms, and the radicals are preferably selected from the group consisting of aryl, aryloxy, alkyl, and alkoxy groups. The more preferred ligands are those consisting of at least one but preferably two or three aryl-and/or aryloxy groups as the organic moieties. For example, preferred modifying ligands are illustrated by the following structural formulae $MR_3$ where M is P, As, or Sb, and R is e.g. phenyl $(C_6H_5-)$, phenoxy $(C_6H_5O-)$, or tolyl $(CH_3(C_6H_4)-)$, xylyl $(CH_3 \cdot C_6H_3 \cdot CH_3)$, e.g., $P(C_6H_5)_3$, $P(C_6H_5O)_3$, As $(C_6H_5)_3$, $Sb(C_6H_5)_3$, $P[CH_3(C_6H_4)]_3$.

The more preferred group of modifying ligands includes the triphenylphosphines, triphenylphosphites, triphenylarsines, and triphenylarsenites. The preferred component is the aryl or aryloxy group, e.g., the phenyl or phenoxy radical. However, the molecule may also contain some aryl groups in addition to the aryloxy radical.

The modifying ligands, and, if desired, other ligands, satisfy the coordination number of the central rhodium atom, and thus form a rhodium-containing cationic complex. The term coordination compound or coordination complex means a compound or complex formed by combination of one or more electronically rich molecules or atoms, e.g., triphenylphosphine, carbon monoxide, 1,5-cyclooctadiene, with one or more electronically poor molecules or atoms, e.g., rhodium.

The rhodium complexes of the present invention are ionic compounds having a non-complexing anionic moiety. These have the general formula $RhL_xAn$. In this formula, the cationic rhodium moiety is $RhL_x^+$ and the non-coordinating anionic moiety $An^-$ is exemplified by $BPh_4^-$, $BF_4^-$, $ClO_4^-$, $PF_6^-$, $NO_3^-$, and $SiF_6^{2-}$.

In the above formulae L is a ligand, (either the same or different ligands as described herein) and $x$ varies from 2 to 5. The ligand L may or may not be a modifying ligand. For example, in the case where $[Rh(Ph_3P)_5]^+$ is employed as the rhodium-containing cation, $Ph_3P$ is the ligand L and it is also a modifying ligand. In the case where $[Rh(COD) (Ph_3P)_2]^+$ is employed as the rhodium-containing cation $Ph_3P$ and COD are the ligands L, but only $Ph_3P$ is a modifying ligand. Finally, in the case were $[Rh(COD)_2]^+$ is employed as the rhodium-containing cation, COD is the ligand L, and at least two moles or a modifying ligand such as $Ph_3P$ is furnished to the reaction solution per mole of rhodium to obtain the catalyst of the present invention. In cases where the ligand L is not a modifying ligand, then it is a ligand displaceable by carbon monoxide under reaction conditions, e.g., COD. Examples of the ligand L include;

mono-enes of 2 to 12 carbon atoms,
dienes of 4 to 12 carbon atoms,
trienes of 6 to 16 carbon atoms,
alkynes of 2 to 12 carbon atoms,
ketones of 3 to 12 carbon atoms,
nitriles of 2 to 12 carbon atoms,
N-alkylamides of 2 to 12 carbon atoms,
N,N-dialkylamides of 3 to 12 carbon atoms,
sulfoxides of 2 to 12 carbon atoms,
tertiary organo phosphorus compounds of 3 to 90 carbon atoms,
tertiary organo arsenic compounds of 3 to 90 carbon atoms,
tertiary organo antimony compounds of 3 to 90 carbon atoms,
carbon monoxide, and combinations thereof.

The ionic rhodium compounds described above are utilized in the present invention as a means of introducing rhodium into the reaction solution and are sometimes referred to as catalyst precursors. Rhodium introduced in this manner together with carbon monoxide, hydrogen, and the modifying ligand described herein form the stable and highly selective rhodium catalysts of the present invention.

The proportions of the rhodium catalyst in the reaction zone, e.g. in the liquid phase relative to the olefin feed are not particularly critical but are chosen so as to maintain a homogeneous liquid medium. In general, higher concentrations of catalysts produce a faster reaction rate. Concentrations of rhodium compounds or complexes in the liquid phase between $10^{-6}$ moles/liter and $10^{-1}$ moles/liter can be used. Higher molar concentrations (i.e. molarities) even to the extent of 1 mole/liter and higher may be used if desired.

In a preferred practice of the invention it is advantageous to add an additional amount of modifying ligand, e.g., an organo phosphorus, organo arsenic, or organo antimony ligand, to the reaction medium in excess of that required to form a stoichiometric rhodium compound or complex containing that ligand, so as to improve catalyst life and to improve selectivity for the formation of straight-chain aldehydes.

In another preferred practice of this invention, the modifying ligand is used as the solvent for the reaction. This practice results in the maximum concentration of this ligand in contact with the rhodium complex and results in improved catalyst life and increased selectivity to the straight-chain aldehyde when α-olefins are employed as feedstocks. This is desired for example, in the manufacture of butryaldehyde which is subsequently transformed to 2-ethylhexanol, a component of plasticizer esters such as 2-ethylhexyl dodecanoate.

In general the liquid reaction medium employed in the catalyst solutions of the present invention can be a high boiling compound. However, mixtures of high boiling compounds may also be used as the liquid medium. These liquids are chemically inert under the reaction conditions, an example of such a liquid being dioctylphthalate. The liquid medium may be hydroxylic compounds, e.g., alcohols such as methanol, ethanol or hexanol; ketones such as acetone or acetophenone; carboxylic acids such as octanoic acid; paraffinic hydrocarbons, including substituted derivatives having from 6 to 30 carbon atoms; and organic esters having the formula $R(CO) (OR')$ where R and R' have from 1 to 15 carbon atoms each. Other solvents include the ortho -phosphorus and orthosilicon esters, having the formula $(R'O)_xM=O$ where M is selected from the group consisting of phosphorus and silicon, and x provides the number of radicals necessary to satisfy the valence of the phosphorus or silicon moiety. Examples of such radicals include methyl, ethyl, propyl, butyl, pentyl, hexyl, heptyl, octyl, nonyl decyl, dodecyl, didecyl, cyclohexyl, phenyl, napthyl, anthracyl, and their various isomeric analogues. The following is a partial list of solvents: dodecane, hexadecane, naphthalene, biphenyl, acetophenone, dioctyl phthalate, dimethyl phthalate, ethyl benzoate, didecyl phthalate, dimethyl adipate, triphenyl phosphate, tricresyl phosphate, dibutylphenyl phosphate, tetramethyl orthosilicate, and tetrabutyl orthosilicate. The feed or substrate, such as dodecene, may be used as a solvent. The product aldehyde of the reaction may also be used as solvent for the reaction.

A particular advantage of providing the hydroformylation catalysts as ionic rhodium compounds of the present invention, such as $Rh(CO)_3(Ph_3P)_2BPh_4$, is the unusual stability of the catalyst thus generated. These compounds yield catalyst which are stable under reduced pressures at elevated temperatures. This factor is of prime importance in the product recovery and liquid phase catalyst recycle stage of the hydroformylation process. Hydroformylation catalyst described in the prior art often undergo substantial decomposition under conditions necessary for product isolation, catalyst recovery, and recycle processing, and are, therefore, less suitable.

In the process of the present invention, the reaction mixture is generally removed from the reaction zone to a separation zone for recovery of residual catalyst solution and separation of the aldehyde product. The present process permits the application of a vacuum for product and reactant separation without decomposition of the rhodium catalysts.

Another advantage of the present process is its ability to produce predominantly straight chain aldehyde products, and substantially no alcohols, paraffins or other by-products even after long use and repeated recycling of the catalyst. Catalysts employed in processes of the prior art generally cause the production of substantial quantities of paraffins, alcohols and/or other undesirable high boiling by-products such as acetals, etc., in addition to the desired aldehydes.

The hydroformylation reaction of the present invention is conducted with olefinically unsaturated feeds of from 2 to 30 carbon atoms including straight-chain and unbranched, internal and alpha olefins as well as substituted olefins.

Illustrative olefinically unsaturated compounds which can be employed as reactants include propylene, 1-butene, 1-pentene 1-hexene, 1-heptene, 1-octene, 1-decene, 1-docecene, 1-octadecene, 2-ethyl 1-hexene, styrene, α methyl styrene, 3-phenyl-1-propene allyl chloride, 1,4-hexadiene, 1,7-octadiene, butadiene, 3-cyclohexyl-1-butene, allyl alcohol, hex-1-en-4-ol, oct-1-en-4-ol, vinyl acetate, allyl acetate, 3-butenyl acetate, vinyl propionate, allyl propionate, allyl butyrate, methyl methacrylate, 3-butenyl acetate, vinyl ethyl ether, vinyl methyl ether, allyl ethyl ether, n-propyl 7-octenoate, 3-butenoic acid, 7-octenoic acid, 3-butenenitrile, 5hexenamide, and the like. Preferred olefinically unsaturated compounds include alkenes, alkyl alkenoates, alkenyl alkanoates, alkenyl alkyl ethers, and alkenols, especially those which contain up to 30 carbon atoms.

When vinyl acetate is employed as the olefinically unsaturated compound the major product is α-acetoxy propionaldehyde with none of the β-isomer being detected.

It has been discovered that a characteristic of the process of this invention is that little or no isomerization of the olefin feedstock occurs; consequently when alpha olefins are the feedstock, the products obtained are predominantly normal and methyl-branched aldehydes rather than the so-called higher branched aldehydes, having side chains such as ethyl-, propyl-, butyl-, etc. For example, when decene 1 is the feed-stock, the principal products are substantially n-undecanal and 2-methyl decanal e.g., less than 1% higher branched aldehydes such as 2-ethylnonanal, and no 2-propyloctanal, 2-butylheptanal, etc. as illustrated below:

$$H_2C=CH-CH_2-CH_2-CH_2-CH_2-CH_2-CH_2-CH_2-CH_3$$
$$\text{decene-1}$$

$$(O=CH)-CH_2-CH_2-CH_2-CH_2-CH_2-CH_2-CH_2-CH_2-CH_2-CH_3$$
$$\text{n-undecanal}$$

$$(O=CH)-\underset{\underset{CH_3}{|}}{CH}-CH_2-CH_2-CH_2-CH_2-CH_2-CH_2-CH_2-CH_3 \quad \text{2-methyl decanal}$$

In contrast the use of a cobalt alkyl phosphine complex such as the cobalt carbonyl phosphine complex having the formula $CO_2(CO)_6[n-C_4H_9)_3P]_2$ gives a product containing paraffins, alcohols and higher branched aldehydes totaling more than the desired normal aldehyde fraction produced. The higher branched aldehydes thus obtained are illustrated below:

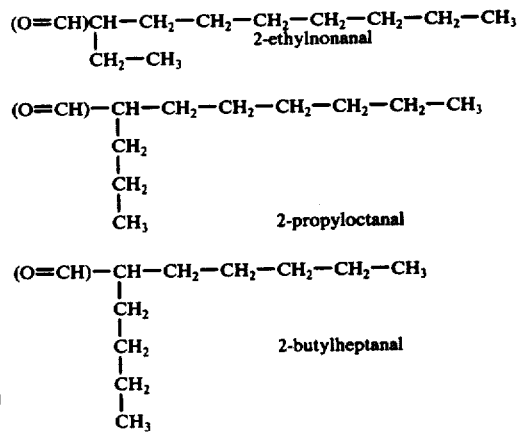

In comparing the present process with processes of the prior art the present rhodium catalyst are superior to the cobalt catalysts and prior art rhodium catalysts, e.g. $RhCl(CO)(Ph_3P)_2$ and $Rh(OAc)(CO)(Ph_3P)_2$, in solubility and one more of the following categories: (a) no olefin isomerization, (b) no olefin hydrogenation, (c)

no aldehyde hydrogenation, (d) lower temperature required for reaction, (e) increased normal product, and (f) high reaction rate under comparable reaction conditions. Furthermore the present process represents an advance over cobalt octacarbonyl process in the greater stability of the catalysts, e.g. during product recovery.

The present invention may be conducted using the catalyst in the liquid phase or dispersed on a porous solid support such as silica, carbon, or alumina. A vapor phase process is carried out with the solid catalysts.

The preparation of two typical rhodium ionic compounds are shown in the following paragraphs.

To a methanol solution (100ml) in a nitrogen atmosphere containing 16 g of $Ph_3P$ (61 mmoles) is added 2.0 g of $[Rh(COD)Cl]_2$ (8.1 mmoles of rhodium), where COD is an abbreviation of 1,5-cyclooctadiene, and the mixture is stirred. After 30 minutes of 3.6 g of $NaBPh_4$(10.5 mmoles) is added and the suspension again stirred for 30 minutes. The fine yellow precipitate is washed with ether and dried. The product is $Rh(COD)(Ph_3P)_2 BPh_4$ as determined by elemental analysis.

A solution of 100 ml of acetone containing 10 g of $Rh(COD)(Ph_3P)_2BPh_4$(10mmoles) is treated with CO and concentrated to a volume of ~10 ml. Crystallization from the acetone is accomplished by the addition of ethanol. The product is filtered and washed with ether in a CO atmosphere. The isolated compound is $Rh(CO)_3(Ph_3P)_2BPh_4$ as demonstrated by elemental analysis, ir, conductivity, and nmr data.

The following examples illustrate specific embodiments of the invention but do not limit the scope of the invention. Example 1 is described in detail, while the other examples employ the procedure of Example 1 with variations of catalysts and reaction conditions. Certain abbreviations are employed such as ~for "about or approximately", Ph for the phenyl group, and CAMP for cyclohexylanisylmethylphosphine.

EXAMPLE 1

A 300 ml batch reactor is charged with a specific number of mmole of an ionic rhodium compound (0.10 mmoles in Ex. 1) and the required amount (10.0 mmoles triphenyl phosphine, $Ph_3P$) of a desired modifying ligand. A solvent (benzene) is added to the reactor which is then closed and flushed three times with $CO/H_2$ gas blend. The reactor and contents are heated to the prescribed reaction temperature (100° C) under about 4.6 $kg/cm^2$ of $CO/H_2$ pressure. The reaction is started by injecting the substrate feedstock (1-hexene) into the reactor and raising the $CO/H_2$ pressure to the prescribed level by further addition. This reactor pressure is maintained by continuously feeding $CO/H_2$ gas blend from a high-pressure reservoir of precisely known volume via a regulator. The rate of reaction is obtained by blotting the pressure of the reservoir as a function of time. When the reaction is complete (i.e., the reservoir pressure does not change with time) the reactor and contents are cooled and the product solution analyzed by gas chromatography.

TABLE 1

| Ex. No. | Catalyst Precursor (mmole) | Ligand (mmole:M)[c] | Solvent (vol. ml) | Temp. (° C) | Olefin (mmole) | Reaction Rate (g mole/ liter·hr.) | Aldehydes Normal/iso Ratio |
|---|---|---|---|---|---|---|---|
| 1[a] | $RhICO(Ph_3P)_2$ (0.10) | $Ph_3P$ (10.0:0.1) | Benzene (100) | 100 | 1-hexene (200) | 0.3 | 3.0 |
| 2[a] | $RhClCO(Ph_3P)_2$ (1.50) | $Ph_3P$ (85:0.85) | Acetophenone (100) | 80 | 1-hexene (660) | 0.3 | 6.7 |
| 3[b] | $RhHCO(Ph_3P)_3$ (0.10) | $Ph_3P$ (1.0:0.01) | Benzene (100) | 80 | 1-hexene (200) | 1.0 | 3.0 |
| 4[a] | Rhodium Black (2.5) | $Ph_3P$ (180:1.80) | Acetophenone (100) | 80 | 1-hexene (200) | 0.3 | 13.2 |

[a]Pressure is 36 $kg/cm^2$ of $CO/H_2$, 1 to 1 mole ratio.
[b]Pressure is 9.5 $kg/cm^2$ of $CO/H_2$, 1 to 1 mole ratio.
[c]Mmole is the number of mmoles of ligand added to the reaction system, and M is the molarity of the ligand in the reaction solution.

TABLE 2

| Ex. No. | Catalyst Precursor (mmole) | Ligand (mmole:M)[b] | Solvent (vol. ml.) | Temp.(° C) and Press. ($kg/cm^2$)[a] | Olefin (mmole) | Reaction Rate (g mole/ liter·hr. | Aldehydes Normal/iso Ratio |
|---|---|---|---|---|---|---|---|
| 5 | $Rh(CO)_3(Ph_3P)_2BPh_4$ (0.10) | $Ph_3P$ (1.0:0.01) | Benzene (100) | 80 (9.5 | 1-hexene (200) | 2.5 | 3.0 |
| 6 | $Rh(CO)_3(Ph_3P)_2BPh_4$ (0.10) | $Ph_3P$ (1.0:0.02) | Benzene (50) | 100 (36) | 1-hexene (170) | 37.0 | 3.0 |
| 7 | $Rh(CO)_3(Ph_3P)_2BPh_4$ (0.70) | $Ph_3P$ (180:1.8) | Acetophenone (100) | 80 (9.5) | 1-hexene (330) | 1.2 | 9.0 |

[a]Mole ratio of $CO/H_2$ is 1 to 1; however, mole ratios of 1 to 10 to 10 to 1 are effective.
[b]See Table 1 for explanation of "mmole:M".

TABLE 3

| Ex. No. | Catalyst Precursor (mmole) | Ligand (mmole:M)[b] | Solvent (vol.ml.) | Temp. (° C) | Olefin (mmole) | Reaction Rate (g mole/ liter·hr.) | Aldehydes Normal/iso Ratio |
|---|---|---|---|---|---|---|---|
| 8 | $Rh(CO)_3(Ph_3P)_2BPh_4$ (0.70) | $Ph_3P$ (180:1.8) | Acetophenone (100) | 80 | 1-hexene (330) | 1.0 (Product Distilled) | 24.0 |
| 9[a] | [Solution from Ex. 8 by distillation] | after aldehyde removed | | 80 | 1-hexene (330) | 1.0 | 24.0 (Product Distilled) |
| 10[a] | [Solution from Ex. 9 by distillation] | after aldehyde removed | | 80 | 1-hexene (330) | 1.5 | 19.0 (Product Distilled) |
| 11[a] | [Solution from Ex. 10 | after aldehyde removed | | 80 | 1-hexene | 1.5 | 24.0 |

TABLE 3-continued

| Ex. No. | Catalyst Precursor (mmole) | Ligand (mmole:M)[b] | Solvent (vol.ml.) | Temp. (°C) | Olefin (mmole) | Reaction Rate (g mole/ liter-hr.) | Aldehydes Normal/iso Ratio |
|---|---|---|---|---|---|---|---|
| | by distillation] | | | | (330) | | |

[a]No additional solvent or rhodium added.
[b]See Table 1 for an explanation of "mmole:M".

The data of Table 1 provide a comparison of representative neutral (non-ionic) rhodium catalyst precursors of the prior art. It is seen that the selectivity to unbranched product and the reaction rates are generally lower than those of Table 2 and Table 3 which are obtained using the catalysts of the present process. Specifically, the selectivities summarized in Examples 8–11 of Table 3 are far superior to any selectivities reported in Table 1. In addition, the best example of the prior art (Example 3, Table 1) exhibits a reactivity of 1.0 and a (normal/iso ratio). This observation is in contrast to what is observed for many catalysts of the prior are which require the use of additional components to stabilize the catalyst during aldehyde distillation. The present process does not require such added stabilizers.

Analysis of the product solution of Examples 1–11 show no evidence for olefin isomerization, i.e. no ethyl- or propyl-branched aldehyde products and no evidence for olefin or aldehyde hydrogenation, i.e., no paraffins or alcohols.

TABLE 4

| Ex. No. | Catalyst Precursor (mmole) | Ligand (mmole:M)[c] | Solvent (vol. ml.) | Temp. (°C) | Olefin (mmole) | Reaction Rate (g mole/ liter-hr.) | Aldehydes Normal/iso Ratio |
|---|---|---|---|---|---|---|---|
| 12[a] | $Rh(CO)_3(CAMP)_2BF_4$ (0.1) | (None:0.0) | Benzene (50) | 100 | 2-hexene (200) | slow | 0.17 |
| 13[b] | $Rh(CO)_3(Ph_3P)_2ClO_4$ (0.5) | $Ph_3P$ (50:0.5) | Acetophenone (100) | 80 | 1-hexene (200) | 0.61 | 6.5 |
| 14[b] | $Rh(CO)_3(Ph_3P)_2PF_6$ (0.5) | $Ph_3P$ (50:0.5) | Acetophenone (100) | 80 | 1-hexene (200) | 0.48 | 6.5 |

[a]Pressure is 36 kg/cm² of $CO/H_2$, 1 to 1 mole ratio.
[b]Pressure is 9.5 kg/cm² of $CO/H_2$, 1 to 1 mole ratio.
[c]See Table 1 for an explanation of "mmole:M".

TABLE 5

| Ex. No. | Catalyst Precursor (mmole) | Ligand (mmole:M)[d] | Solvent (vol. ml.) | Temp. (°C) | Olefin (mmole) | Reaction Rate (g mole/ liter-hr.) | Aldehydes Normal/iso Ratio |
|---|---|---|---|---|---|---|---|
| 15[a] | $Rh(CO)_3(Ph_3P)_2BPh_4$ (0.1) | $P(OMe)_3$ (160:1.6) | Acetophenone (100) | 80 | 1-hexene (620) | 0.1 | — |
| 16[b] | $Rh(CO)_3(Ph_3P)_2BPh_4$ (0.5) | $P(OEt)_3$ (100:1.0) | Benzene (100) | 125 | isomerized octene (200) | 0.1 | — |
| 17[b] | $Rh(CO)_3(Ph_3P)_2BPh_4$ (0.1) | $P(O-n-Butyl)_3$ (10:0.1) | Benzene (100) | 100 | 1-hexene (200) | 0.1 | 4.0 |
| 18[b] | $Rh(CO)_3(Ph_3P)_2BPh_4$ (0.37) | $P(O-n-Butyl)_3$ (50:0.5) | Benzene (100) | 125 | isomerized octene (200) | 0.1 | — |
| 19[b] | $Rh(CO)_3(Ph_3P)_2BPh_4$ (0.1) | $P(n-Butyl)_3$ (10:0.1) | Benzene (100) | 100 | 1-hexene (200) | 0.9 | 2.3 |
| 20[a] | $Rh(CO)_3(Ph_3P)_2BPh_4$ (0.5) | Diphes[c] (5:0.05) | Benzene (100) | 100 | 1-octene (200) | 0.8 | 0.9 |
| 21[b] | $Rh(CO)_3(Ph_3P)_2BPh_4$ (0.1) | $(PhO)_3P$ (10:0.2) | Benzene (50) | 100 | 1-hexene (200) | 25. | 3.0 |

[a]Pressure is 9.5 kg/cm² of $CO/H_2$, 1 to 1 mole ratio.
[b]Pressure is 36 kg/cm² of $CO/H_2$, 1 to 1 mole ratio.
[c]$Ph_2P-CH_2-CH_2-PPh_2$.
[d]See Table 1 for an explanation of "mmole:M".

normal to iso ratio of 3.0 while the rhodium catalyst of this invention (Example 5, Table 2) shows a reactivity of 2.5 which is 250% as great with no loss in selectivity (i.e., normal/iso ratio) to unbranched aldehyde product.

When example 7 is repeated using catalyst precursors which contain cyclooctene, e.g. $[Rh(C_8H_{14})_2(Ph_3P)_2]BPh_4$; 1,5-cyclooctadiene, e.g. $[Rh(C_8H_{12}) (Ph_3P)_2]BPh_4$; 1,5,9-cyclododecatriene, e.g. $[Rh(C_{12}H_{18}) (Ph_3P)_2]BPh_4$; diphenylacetylene, e.g. $[Rh(C_6H_5C\equiv CC_6H_5)_3(Ph_3P)_2]BPh_4$; acetone, e.g. $[Rh(acetone)_2(Ph_3P)]BPh_4$; benzonitrile, e.g. $[Rh(C_6H_5CN)_2(Ph_3P)_2]BPh_4$; N,N-dimethylformamide (DMF), e.g. $[Rh(DMF)_2(Ph_3P)_2]BPh_4$; and dimethylsulfoxide (DMSO), e.g. $[Rh(DMS)_2(Ph_3P)_2]BPh_4$, similar results are obtained. The Examples in Table 3 show that the catalyst may be recycled without loss of catalytic activity or selectivity to unbranched aldehydes The data of Table 4 show that in addition to ionic rhodium compounds containing the non-coordinating anion tetraphenylborate, complexes containing other non-corrdinating anions (e.g. tetrafluoroborate, perchlorate, and hexafluorphosphate) are also effective precursors for the catalysts of the present hydroformylation process. Other non-corrdinating anions such as nitrates are also effective in tests using similar conditions. No paraffins or alcohols are formed in Examples 12–14. In addition, the product solutions of Examples 13 and 14 contain no ethyl-or propyl-branched aldehydes.

The data of Table 5 show the use of excess phosphines and phosphites with the aryl phosphine and aryl phosphites being most effective, and with the alkyl phosphines being more effective than the alkyl phosphites.

No paraffins or alcohols are formed in Example 15–21, while examples employing isomerized olefin feed (Examples 16 and 18) necessarily yield higher branched aldehydes, i.e. ethyl- and propyl-branched aldehydes; no higher branched aldehydes are produced in Example 15, 17, 19, 20 and 21.

or propyl-branched aldehydes observed except with isomerized feeds.

The data of Table 7 show a variety of solvents or reaction media useful in the practice of the invention, although a solvent is not necessary.

The data of Table 8 show the effect of using excesses

TABLE 6

| Ex. No. | Catalyst Precursor (mmole) | Ligand (mmole:M)[c] | Solvent (vol. ml.) | Press (kg/cm$^2$) | Olefin (mmole) | Reaction Rate (g mole/liter-hr.) | Aldehydes Normal/iso Ratio |
|---|---|---|---|---|---|---|---|
| 22[a] | Rh(CO)$_3$(Ph$_3$P)$_2$BPh$_4$ (0.1) | Ph$_3$P (3.3:0.07) | Benzene (50) | 9.5 | 1-hexene (200) | 1.1 | 3.2 |
| 23[a] | (Rh(CO)$_3$(Ph$_3$P)$_2$BPh$_4$ (0.1) | Ph$_3$P (3.3:0.07) | Benzene (50) | 72 | 1-hexene (200) | 0.75 | 2.9 |
| 24[a] | Rh(CO)$_3$(Ph$_3$P)$_2$BPh$_2$ (0.1) | Ph$_3$P (3.3:0.07) | Benzene (50) | 36 | 1-hexene (200) | 0.4 | 2.9 |
| 25[b] | Rh(CO)$_3$(Ph$_3$P)$_2$BPh$_4$ (0.65) | Ph$_3$P (87:0.87) | Acetophenone (100) | 9.5 | 1-hexene (330) | 2.2 | 15.7 |
| 26[b] | Rh(CO)$_3$(Ph$_3$P)$_2$BPh$_4$ (0.65) | Ph$_3$P (37:0.87) | Acetophenone (100) | 36 | 1-hexene (330) | 2.0 | 4.4 |
| 27[b] | Rh(CO)$_3$(Ph$_3$P)$_2$BPh$_4$ (0.65) | Ph$_3$P (87:0.87) | Acetophenone (100) | 72 | 1-hexene (330) | 1.1 | 4.8 |

[a]Temperature is 60° C.
[b]Temperature is 80° C.
[c]See Table 1 for an explanation of "mmole:M"

TABLE 7

| Ex. No. | Catalyst Precursor (mmole) | Ligand (mmole:M)[c] | Solvent (vol. ml.) | Temp. (° C) | Olefin (mmole) | Reaction Rate (g mole/liter-hr.) | Aldehydes Normal/iso Ratio |
|---|---|---|---|---|---|---|---|
| 28[a] | Rh(CO)$_3$(Ph$_3$P)$_2$BPh$_4$ (0.1) | Ph$_3$p (3.3:0.07) | Acetic Acid (50) | 80 | 1-hexene (200) | 0.7 | 2.6 |
| 29[b] | Rh(CO)$_3$(Ph$_3$P)$_2$BPh$_4$ (0.1) | Ph$_3$P (85:0.85) | Acetophenone (100) | 60 | 1-hexene (660) | 0.14 | 5.7 |
| 30[a] | Rh(CO)$_3$(Ph$_3$P)$_2$BPh$_4$ (0.65) | Ph$_3$P (7.6:0.08) | Dodecane (100) | 150 | isomerized dodecene (120) | 0.8 | 0.22 |
| 31[b] | Rh(CO)$_3$(Ph$_3$P)$_2$BPh$_4$ (0.65) | Ph$_3$P (87:0.87) | 1-Dodecane (also a reactant) (100) | 100 | 1-dodecene (500) | 2.5 | 6.7 |
| 32[b] | Rh(CO)$_3$(Ph$_3$P)$_2$BPh$_4$ (0.1) | Ph$_3$P (10:0.1) | Methanol (100) | 80 | styrene[d] (200) | 1.0 | 7.6 |

[a]Pressure is 36 kg/cm$^2$ of CO/H$_2$, 1 to 1 mole ratio.
[b]Pressure is 9.5 kg/cm$^2$ of CO/H$_2$, 1 to 1 mole ratio.
[c]See Table 1 for an explanation of "mmole:M".
[d]Product is a mixture of phenyl propionaldehydes.

TABLE 8

| Ex. No. | Catalyst Precursor (mmole) | Ligand (mmole:M)[c] | Solvent (vol. ml.) | Olefin (mmole) | Reaction Rate (g mole/liter-hr.) | Aldehydes Normal/iso Ratio |
|---|---|---|---|---|---|---|
| 33[a] | Rh(CO)$_3$(Ph$_3$P)$_2$BPh$_4$ (0.1) | Ph$_3$P (85:0.85) | Acetophenone (100) | 1-hexene (660) | 0.9 | 7.4 |
| 34[a] | Rh(CO)$_3$(Ph$_3$P)$_2$BPh$_4$ (0.1) | Ph$_3$P (176:1.76) | Acetophenone (100) | 1-hexene (660) | 0.3 | 24 |
| 35[a] | Rh(CO)$_3$(Ph$_3$P)$_2$BPh$_2$ (0.1) | Ph$_3$P (45:0.9) | Acetophenone (50) | 1-hexene (330) | 1.4 | 6.7 |
| 36[a] | Rh(CO)$_3$(Ph$_3$P)$_2$BPh$_4$ (0.65) | Ph$_3$P (176:1.76) | Acetophenone (100) | 1-hexene (310) | 0.5 | 24 |
| 37[a] | Rh(CO)$_3$(Ph$_3$P)$_2$BPh$_4$ (0.1) | Ph$_3$P (85:0.85) | Benzene (100) | 1-hexene (470) | 0.9 | 7.4 |
| 38[a] | Rh(CO)$_3$(Ph$_3$P)$_2$BPh$_4$ (1.65) | Ph$_3$P (85:0.85) | Acetophenone (100) | 1-hexene (660) | 3.3 | 9.0 |
| 39[a] | Rh(CO)$_3$(Ph$_3$P)$_2$BPh$_4$ (.65) | Ph$_3$P (22:0.44) | Acetophenone (50) | 1-hexene (330) | 10.8 | 5.6 |
| 40[b] | Rh(CO)$_3$(Ph$_3$P)$_2$BPh$_4$ (0.1) | (None:0.0) | Benzene (50) | 1-hexene (200) | ~ 50. | 1.6 |

[a]Pressure is 9.5 kg/cm$^2$ of CO/H$_2$, 1 to 1 mole ratio; temperature is 80° C.
[b]Pressure is 36 kg/cm$^2$ of CO/H$_2$, 1 to 1 mole ratio; temperature is 100° C.
[c]See Table 1 for an explanation of "mmole:M".

The data in Table 6 show the lower pressures give superior selectivity to straight-chain aldehydes. No paraffin or alcohols are formed in the examples of Tables 6, 7, 8 nor are higher branched products, i.e. ethyl- of modifying ligands on the rate and selectivity. The higher molar excesses of ligands increase the selectivity to normal products (relative to the last example with zero excess modifying ligand).

TABLE 9

| Ex. No. | Catalyst Precursor (mmole) | Ligand (mmole:M)[f] | Solvent (vol. ml.) | Temp. (° C) | Olefin (mmole) | Reaction Rate (g mole/ liter-hr.) | Aldehydes Normal/iso Ratio |
|---|---|---|---|---|---|---|---|
| 41[a] | $Co_2(CO)_8$ (5) | $Ph_3P$ (20:0.2) | Benzene (100) | 195[b,c,d] | isomerized octenes (200) | slow | 0.96 |
| 42[a] | $Ir(CO)_3(Ph_3P)_2BPh_4$ (0.5) | (None:0.0) | Benzene (100) | 150[b,d] | isomerized octenes (200) | 0.4 | 0.05 |
| 43[a] | $Ir(CO)_2acac$ (0.5) | (None:0.0) | Benzene (100) | 150[b,d] | isomerized octenes (200) | 1.5 | 0.1 |
| 44[e] | $Rh(CO)_2acac$ (0.1) | $Ph_3P$ (0.1:0.002) | Benzene (50) | 60 | 1-hexene (200) | 0.5 | 1.3 |
| 45[e] | $Rh(CO)_3(Ph_3P)_2BPh_4$ (0.1) | $Ph_3P$ (3.3:0.07) | Benzene (50) | 60 | 1-hexene (200) | 0.5 | 3.0 |
| 46[e] | $Rh(OAc)(CO)(n-butyl_3P)_2$ (0.1) | (n-butyl)$_3$P (1.3:0.01) | Benzene (100) | 80 | 1-hexene (200) | 1.6 | 2.3 |

[a]Pressure is 36 kg/cm² of CO/H₂, 1 to 1 mole ratio.
[b]No reaction at 100° C.
[c]Substantial alcohol production.
[d]Substantial olefin reduction to paraffin.
[e]Pressure is 9.5 kg/cm² of CO/H₂, 1 to 1 mole ratio.
[f]See Table 1 for an explanation of "mmole:M".

TABLE 10

| Ex. No. | Catalyst Precursor (mmole) | Ligand (mmole:M)[g] | Solvent (vol. ml.) | Temp. (° C) | Olefin (mmole) | Reaction Rate (g mole/ liter-hr.) | Aldehydes Normal/iso Ratio |
|---|---|---|---|---|---|---|---|
| 47[a] | $Rh(CO)_3(Ph_3P)_2BPh_4$ (0.5) | $Ph_3P$ (20:0.2) | Benzene (100) | 125 | α-methyl styrene[h] (500) | 1.0 | 19. |
| 48[a] | $Rh(CO)_3(Ph_3P)_2BPh_4$ (0.5) | $Ph_3P$ (10:0.1) | Benzene (100) | 125 | ethyl vinyl ether (200) | 3.0 | 5. |
| 49[b] | $Rh(CO)_3(Ph_3P)_2BPh_4$ (0.5) | $Ph_3P$ (10:0.1) | Acetophenone (100) | 80 | ethylene (180) | very fast | c |
| 50[a] | $Rh(CO)_3(Ph_3P)_2BPh_4$ (0.1) | $Ph_3P$ (3.3:0.07) | Benzene (50) | 80 | propylene (140) | 1.0 | 3.0 |
| 51[a] | $Rh(CO)_3(Ph_3P)_2BPh_4$ (0.2) | $Ph_3P$ (0.68:0.007) | Benzene (100) | 100 | vinyl acetate (400) | 1.0 | d |
| 52[a] | $Rh(CO)_3(Ph_3P)_2BPh_4$ (0.65) | $Ph_3P$ (2.0:0.02) | Acetophenone (100) | 125 | isomerized pentenes (180) | 3.8 | 0.9[e] |
| 53[a] | $Rh(CO)_3(Ph_3P)_2BPh_4$ (0.5) | $Ph_3P$ (10:0.1) | Benzene (100) | 100 | ethyl acrylate (200) | 0.7 | ~0.5 |
| 54[a] | $Rh(CO)_3(Ph_3P)_2BPh_4$ (0.1) | (None :0.0) | Benzene (100) | 100 | iso-butylene (300) | 0.5 | f |
| 55[b] | $Rh(CO)_3(Ph_3P)_2BPh_4$ (0.5) | $Ph_3P$ (150 :1.5) | Benzene (100) | 100 | 1,5-hexadiene (290) | 0.6 | 1.3 |

[a]Pressure is 36 kg/cm² CO/H₂, 1 to 1 mole ratio.
[b]Pressure is 9.5 kg/cm² CO/H₂, 1 to 1 mole ratio.
[c]Only straight-chain product possible.
[d]The major product is acetoxy propionaldehyde which is comprised of 100% of the α-isomer.
[e]Product composition: 7.8 mole % n-hexanal, 41.2 mole % 2-methyl pentanal, 51 mole % 2-ethyl butanal.
[f]No (CH₃)₃C—CHO observed.
[g]See Table 1 for an explanation of "mmole:M".
[h]Product is a mixture of phenyl butyraldehydes.

The data of Table 9 show various catalysts of the prior art. It is noted that an iridium cationic complex is a far less effective catalyst precursor than the rhodium cationic complexes of the present invention. It is also found that iridium and cobalt compounds have the undesirable characteristic of hydrogenating olefin feed (with cobalt also hydrogenating the product aldehydes to alcohols).

Data are also shown for rhodium and iridium acetylacetonates (Examples 43 and 44) which exhibit inferior selectivities relative to the rhodium catalysts of the present invention (Example 45).

The data of Table 10 show various substrates (feedstocks) used with the present rhodium catalysts. Other substrates which yield aldehydes in the present process include 1-butene, 1-pentene, 1-hexene, 1-heptene, 1-decene, 1-octadecene, 2-ethyl-1-hexene, 3-phenyl-1-propene, allyl chloride, 1,4-hexadiene, 1,7-octadiene, butadiene, 3-cyclohexyl-1-butene, allyl alcohol, hex-1-en-4-ol, oct-1-en-4-ol, allyl acetate, 3-butenyl acetate, vinyl propionate, allyl propionate, allyl butyrate, methyl metacrylate, 3-butenyl acetate, vinyl methyl ether, allyl ethyl ether, n-propyl 7-octenoate, 3-butenoic acid, 3-butene-nitrile, 5-hexenamide, and allyl alkenoates, alkenyl alkanoates, alkenyl alkyl ethers, and alkenols, especially those which contain up to 30 carbon atoms.

The data summarized in Table 11 shows that the use of triphenylphosphine, which is exemplary of phosphines as the solvent for the hydroformylation reaction gives an unexpectedly high yield of unbranched aldehyde products when used with the cationic complex. Compare Example 62 which yields over 90% normal butanal with the other examples employing Rh COD(PH₃P)₂BPh₄ as a catalyst for the reaction.

TABLE 11

| Ex. No. | Catalyst Precursor (mmole) | Ligand (mmole:M)[c] | Solvent (vol.ml) | Temp.(° C) Pressure[a] (kg/cm²) | Reaction Rate (g-mole/liter-hr. | Aldehydes Normal/iso Ratio |
|---|---|---|---|---|---|---|
| 56 | $Rh(COD)(Ph_3P)_2BPh_4$ (0.1) | $Ph_3P$ (10:0.1) | Benzene (100) | 80° 9.5 | 1.3 | 2.3 |
| 57 | $Rh(CO)_2Cl)_2$ | (None:0.0) | Acetophone | 100° | 3.3 | 0.85 |

TABLE 11-continued

| Ex. No. | Catalyst Precursor (mmole) | Ligand (mmole:M)[c] | Solvent (vol.ml) | Temp.(° C) Pressure[a] (kg/cm$^2$) | Reaction Rate (g-mole/liter-hr.) | Aldehydes Normal/iso Ratio |
|---|---|---|---|---|---|---|
| 58 | $Rh_4(CO)_{12}$ (0.05) (0.025) | (None:0.0) | Benzene (100) | 36 80° 9.5 | 0.3 | .7 |
| 59 | $Rh(COD)(Ph_3P)_2BPh_4$ (0.1) | $Ph_3P$ (100:1.00) | Benzene (100) | 80° 9.5 | 0.3 | 4.0 |
| 60 | $Rh(COD)(Ph_3P)_2BPh_4$ (0.5) | $Ph_3P$ (384:4.56) | $Ph_3P$[b] | 85° 9.5 | 0.3 | 5.6 |
| 61 | $Rh(COD)(Ph_3P)_2BPh_4$ (0.1) | $Ph_3P$ (100:1.0) | Benzene (100) | 80° 72 | 0.2 | 2.3 |
| 62 | $Rh(COD)(Ph_3P)_2BPh_4$ (0.5) | $Ph_3P$ (400:4.56) | $Ph_3P$[b] | 120° 3.9 | 14.0 | 10.1 |
| 63 | $Rh(COD)(Ph_3P)_2BPh_4$ (0.7) | $Ph_3P$ (87:0.87) | Acetophenone (100) | 80° 9.5 | 0.3 | 4.5 |
| 64 | $Rh(COD)(Ph_3P)_2BPh_4$ (0.7) | $(Ph_3P)$ (87:0.87) | Acetophenone (100) | 100° 9.5 | 1.0 | 3.2 |
| 65 | $Rh(COD)(Ph_3P)_2BPh_4$ (0.1) | $Ph_3P$ (172:1.72) | Benzene (100) | 100° 9.5 | 0.8 | 4.9 |
| 66 | $Rh(COD)(Ph_3P)_2BPh_4$ (0.1) | $Ph_3P$ (1.0:0.1) | Benzene (100) | 80° 9.5 | 4.0 | 2.0 |
| 67 | $Rh(COD)(Ph_3P)_2BPh_4$ (0.7) | $Ph_3P$ (176:2.48) | Acetophenone (100) | 80° 9.5 | 0.5 | 6.1 |

[a]Initial pressure of CO and $H_2$, mole ratio 1 to 1.
[b]The ligand $Ph_3P$ is the solvent for this reaction.
[c]See Table 1 for an explanation of "mmole:M".

EXAMPLE 68

A 300 ml batch reactor is charged with 0.1 mmole of [Rh(COD) (Ph$_3$As)$_2$]+ClO$_4$— as the catalyst precursor (where "COD" represents 1,5-cyclooctadiene) and 100 mmoles of Ph$_3$As, triphenyl arsine as the modifying ligand. One hundred milliliters of benzene is added to the reactor which is then closed and flushed three times with an equimolar CO/H$_2$ gas blend. The reactor and contents are heated to 100° C under about 4.6 kg/cm$^2$ pressure of the CO/H$_2$ gas mixture. The reaction is started by injecting 21 gms. (0.25 mole) of hexene-1-feedstock into the reactor and raising the CO/H$_2$ pressure to 46. kg/cm$^2$ by further addition of the CO/H$_2$ gas blend. This reactor pressure is maintained by continuously feeding CO/H$_2$ gas blend from a high-pressure reservoir of a known volume via a regulator. The rate of reaction is determined by plotting the pressure of the reservoir as a function of time and is found to be ca. 13 g-mole/1-hr (gram-moles per liter-hour) in this case. When the reaction is complete (i.e., the reservoir pressure does not change with time) the reactor and its contents are cooled and the product solution analyzed by gas chromatography. In this case the product contained ca. 0.22 mole of C$_7$-aldehydes with ca. 78% of these being the normal (completely linear) isomer. The remaining 22% is 2-methylhexana. The product solution is virtually free of other branched aldehydes, e.g., 2-ethylpentanal, alcohols, and alkanes. The results of this experiment are tabulated as Example 68 in Table 12 for comparative purposes with the other examples.

EXAMPLES 69 – 75

These examples are preformed using a procedure which is similar to that described in Example 68. The data of these examples are tabulated in Table 12.

TABLE 12

Hydroformylation of Hexene-1 Using Benzene as the Solvent

Catalyst Precursor = [Rh(COD)(Ph$_3$As)$_2$]+ClO$_4$−, 0.1 mmole
Solvent = Benzene, 100 ml
Substrate Charge = 21 g. or 0.25 mole of hexene-1
Ligand Charge = 100 mmoles
(Ph$_3$As or Ph$_3$Sb)
Gas Blend = 50/50 vol. % CO/H$_2$

| Example | Ligand | Temp. (° C) | Press (kg/cm$^2$) | Gas Uptake (moles) | Rate (g-mole/ liter-hr) | % Normal Aldehyde |
|---|---|---|---|---|---|---|
| 68 | Ph$_3$As | 100 | 46. | 0.44 | ~13 | 78% |
| 69 | Ph$_3$As | 100 | 46. | 0.42 | ~13 | 78% |
| 70 | Ph$_3$As | 100 | 18.4 | 0.32 | " | 78% |
| 71 | Ph$_3$As | 100 | 9.2 | 0.29 | 0.7 | 76% |
| 72 | Ph$_3$Sb | 100 | 46. | 0.37 | 0.8 | 81% |
| 73 | Ph$_3$Sb | 80 | 46. | 0.25 | 0.4 | 83% |
| 74 | Ph$_3$Sb | 100 | 9.2 | 0.23 | 0.7 | 84% |
| 75 | Ph$_3$Sb | 80 | 9.2 | 0.18 | 0.3 | 86% |

EXAMPLE 76

A 300 ml batch reactor is charged with 0.5 mmole of [Rh(COD) (Ph$_3$As)$_2$]+ClO$_4$— as the catalyst precursor and 105 gms. (343 mmoles) of Ph$_3$As as the modifying ligand and the solvent. The reactor is then closed, flushed, and heated at 100° C as described in Example 68. The reaction is started by injecting 21 gms. (0.25 mole) of hexene-1 into the reactor and raising the 50/50 vol. % CO/H$_2$ pressure to 46 kg/cm$^2$ by further addition of the CO/H$_2$ gas blend. The reaction pressure is maintained and the reaction rate determined as described in Example 68. The reaction rate is ca. 14g mole/1-hr. When the reaction is complete the reactor and its contents are cooled to ca. 70° C whereupon 50 ml. of benzene are injected into the reactor in order to keep the contents from solidifying. After reaching room temperature, the benzene solution is withdrawn and analyzed by gas chromatography, indicating 0.25 moles of C$_7$-aldehydes with ca. 79% normal (linear) isomer. Use of the corresponding arsenite compound, [Rh(COD)[As- (OPh)₃]₂]ClO₄; in conjunction with free triphenylaresenic as the modifying ligand, also results in a hydroformylation catalyst. This can be done either using a solvent such as benzene or the triphenylarsenite ligand as the solvent.

EXAMPLE 77

This experiment is carried out in a manner similar to that described in Example 76 except 105 gms. of Ph₃Sb (298 mmoles is used as the modifying ligand and solvent instead of Ph₃As, and the reaction is run at 120° C and 9.2 kg/cm² of 50/50 vol. % CO/H₂ gas blend. The reaction rate is very much slower (0.1 g-mole/liter-hr) and analysis of the product solution indicates the C₇-aldehyde contain 88% of the normal (linear) isomer. Use of the corresponding stibite compound [Rh(COD)[Sb(OPh)₃]₂]ClO₄; in conjunction with free triphenylstibite as the modifying ligand also results in a hydroformylation catalyst. This can be done either using a solvent such as benzene or the triphenylstibite ligand as the solvent.

What is claimed is:

1. In an improved process for the production of aldehydes, by the reaction of a olefinically insaturated hydrocarbon having from 2 to 30 carbon atoms, carbon monoxide, and hydrogen at a total pressure of from 4.6 to 142 kg/cm², and at a temperature of from about 60° C to about 180° C, the improvement which comprises contacting the said reactants in the presence of a solution of a rhodium catalyst, in which said catalyst is provided by (1) introducing rhodium into the reaction solution in the form of an ionic rhodium compound, the said ionic compound consisting of (a) a rhodium-containing cation having rhodium comlexed with ligands selected form the group consisting of:

mono-enes of 2 to 12 carbon atoms,
dienes of 4 to 12 carbon atoms,
trienes of 6 to 16 carbon atoms,
alkynes of 2 to 12 carbon atoms,
ketones of 3 to 12 carbon atoms,
nitriles of 2 to 12 carbon atoms,
N-alkylamides of 2 to 12 carbon atoms,
N,N-dialkylamides of 3 to 12 carbon atoms,
sulfoxides of 2 to 12 carbon atoms,
tertiary phosphines and phosphites of 3 to 90 carbon atoms,
tertiary arsines and arsenites of 3 to 90 carbon atoms,
tertiary stibines and stibites of 3 to 90 carbon atoms,
carbon monoxide, and combinations thereof, and (b) BPh₄⁻; and (2) furnishing to the reaction solution at least two moles of a modifying ligand per mole of ionic rhodium compound where the modifying ligand is furnished either pre-coordinated in the said ionic rhodium compound or as a free compound; and where the modifying ligand, is selected from the group consisting of tertiary phosphines and phosphites, arsines and arsenites, stibines, and stibites, having from 3 to 90 carbon atoms.

2. Process as in claim 1 in which the modifying ligand is present at a concentration of rom 0.0001 to 10 molar in excess of the ionic rhodium compound.

3. Process as in claim 1 in which the modifying ligand is present at a concentration of from 0.0001 to 0.001 molar in excess of the ionic rhodium compound.

4. Process as in claim 1 in which the modifying ligand is present at a concentration of from 0.001 to 10 molar in excess of the ionic rhodium compound.

5. Process as in claim 1 in which the modifying ligand is present at a concentration of from 0.01 to 0.1 molar in excess of the ionic rhodium compound.

6. Process as in claim 1 in which the modifying ligand is present at a concentration of from 0.1 to 1 molar in excess of the ionic rhodium compound.

7. Process as in claim 1 in which the modifying ligand is triphenylphosphine and is present at a concentration of from 0.01 to 0.1 molar in excess of the ionic rhodium compound.

8. Process as in claim 1 in which the modifying ligand is triphenylphosphine and is present at a concentration of from 0.1 to 2.5 molar in excess of the ionic rhodium compound.

9. Process as in claim 1 where the modifying ligand is the solvent for the reaction system.

10. Process as in claim 1 where the modifying ligand is triphenylphosphine and is the solvent for the reaction system.

11. Process as in claim 1 in which the total pressure of carbon monoxide and hydrogen is from 4.6 to 36 kg/cm².

12. Process as in claim 1 in which the rhodium ionic compound is provided by [Ph(CO)₃(Ph₃P)₂]BPh₄.

13. Process as in claim 1 in which the rhodium ionic compound is provided by a compound selected from the group consisting of [Rh(CO)₃(Ph₃P)₂]BPh₄, [Rh(CO)₃(Ph₃As)₂]BPh₄, and [Rh(CO)₃(Ph₃Sb)₂]BPh₄.

14. Process as in claim 1 in which the modifying ligand is an alkyl phosphine having from 3 to 90 carbon atoms.

15. Process as in claim 1 in which the modifying ligand is an aryl phosphine or phosphite having from 3 to 90 carbon atoms.

16. Process as in claim 1 in which the modifying ligand is triphenyl phosphine or triphenyl phosphite.

17. Process as in claim 1 in which the modifying ligand is an aryl arsine or arsenite having from 3 to 90 carbon atoms.

18. Process as in claim 1 in which the modifying ligand is triphenyl arsine or triphenyl arsenite.

19. Process as in claim 1 in which the modifying ligand is an aryl stibine or stibite having from 3 to 90 carbon atoms.

20. Process as in claim 1 in which the modifying ligand is triphenyl stibine or triphenyl stibite.

21. The process of claim 1 in which the rhodium compound is represented

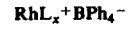

$$RhL_x^+ BPh_4^-$$

in which L represents ligand and $x$ varies from 2 to 5.

22. Process as in claim 1 in which the olefinically unsaturated compound is ethylene and the product is propionaldehyde.

23. Process as in claim 1 in which the olefinically unsaturated compound is propylene and the product is butyraldehy.

24. Process as in claim 1 in which the olefinically unsaturated compound is isomerized pentenes and the product is hexanaldehydes.

25. Process as in claim 1 in which the olefinically unsaturated compound is hexene and the product is heptanaldehydes.

26. Process as in claim 1 in which the olefinically unsaturated compound is dodecene and the product is tridecanalde hydes.

27. Process as in claim 1 in which the olefinically unsaturated hydrocabon have from 6 to 12 carbon atoms and the produced aldehydes have from 7 to 13 carbon atoms.

28. Process as in claim 1 in which the olefinically unsaturated compound is α-methylstyrene and the product is phenyl butyraldehyde.

29. Process as in claim 1 in which the olefinically unsaturated compound is styrene and the product is phenyl propionaldehyde.

* * * * *